United States Patent [19]
Sacchettini et al.

[11] Patent Number: 5,837,732
[45] Date of Patent: Nov. 17, 1998

[54] ANTIMYCOBACTERIAL COMPOUNDS AND METHOD OF USING SAME

[75] Inventors: James Sacchettini, College Station, Tex.; John Blanchard, Pelham Manor, N.Y.; William R. Jacobs, City Island, N.Y.; Robert Bittman, Roslyn Heights, N.Y.

[73] Assignees: Albert Einstein College of Medicine of Yeshiva University, New York; The Research Foundation of the City University of New York, Bronx, both of N.Y.

[21] Appl. No.: 766,273

[22] Filed: Dec. 13, 1996

Related U.S. Application Data

[63] Continuation of Ser. No. 598,085, Feb. 7, 1996, abandoned, which is a continuation-in-part of Ser. No. 386,917, Feb. 7, 1995, Pat. No. 5,648,392, which is a continuation-in-part of Ser. No. 234,011, Apr. 28, 1994, Pat. No. 5,702,935, and Ser. No. 307,376, Sep. 16, 1994, abandoned.

[51] Int. Cl.$^6$ ..................................................... A61K 31/20
[52] U.S. Cl. ........................................... 514/560; 514/924
[58] Field of Search ..................................... 514/560, 924

[56] References Cited

PUBLICATIONS

"Inactivation of General Acyl–CoA Dehydrogenase from Pig Kidney by 2–Alkynoyl Coenzyme A Derivatives: Initial Aspects" by Freund, et al. *Biochemistry* 1985, 24, pp. 5996–6000, 6002.

Medne et al, News of the Latvian SSR Academy of Sciences 7(264) pp. 139–140, 1969.

Merck Manual, p. 126, 1987.

CA 95: 81103, Kuman et al, 1981.

CA 71: 99218, Medne et al, 1969.

*Primary Examiner*—Rebecca Cook
*Attorney, Agent, or Firm*—Amster, Rothstein & Ebenstein

[57] ABSTRACT

The present invention provides a compound having the structure:

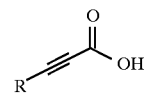

wherein R is a branched or unbranched C1–C30 alkyl, alkenyl or alkynl; or a branched or unbranched C1–C30 alkyl, alkenyl or alkynl substituted with S, O, N, P, $SO_2$, F, Cl, Br, or I, wherein S, O, N, P, or $SO_2$ replaces at least one —$CH_2$—, and F, Cl, Br, or I replaces at least one H. The present invention also provides a pharmaceutical composition comprising the compound above, as well as a method for treating a mycobacterial disease or infection in a subject in need of such treatment by administering to the subject an effective amount of the compound above.

2 Claims, 1 Drawing Sheet

ANTIMYCOBACTERIAL COMPOUNDS AND METHOD OF USING SAME

This application is continuation of application Ser. No. 08/598,085, filed Feb. 7, 1996, abandoned which is a continuation-in-part of application Ser. No. 08/386,917, filed Feb. 7, 1995, now U.S. Pat. No. 5,648,392 which is a continuation-in-part of application Ser. No. 08/234,011, now U.S. Pat. No. 5,702,935 filed Apr. 28, 1994, and application Ser. No. 08/307,376, filed Sep. 16, 1994, abandoned the contents of which are incorporated by reference herein.

STATEMENT OF GOVERNMENT INTEREST

This invention was made with government support under Grant Nos. NIH AI30189 and AI36849. As such, the government has certain rights in this invention.

BACKGROUND OF THE INVENTION

Mycobacteria represents major pathogens of man and animals. For example, *tuberculosis* is generally caused in humans by *Mycobacterium* (*M.*) *tuberculosis* and in cattle by *M. bovis* (which can be transmitted to humans to cause *tuberculosis*). *Tuberculosis* remains widespread and is an important public health problem, particularly in developing countries. It is estimated that there are approximately 10 million cases of *tuberculosis* worldwide, with an annual mortality rate of 3 million.

Cases of disease caused by *M. tuberculosis* and other mycobacteria such as *M. avium-intracellulare* complex (MAC) are increasing as the numbers of immunocompromised individuals is increasing. For example, both *M. tuberculosis* and *M. avium-intracellulare* represent major opportunistic pathogens of patients with acquired immunodeficiency syndrome (AIDS). Kochi, A., Governmental Intervention Programs in HIV/Tuberculosis Infection: Outline of Guidelines for National Tuberculosis Control Programs in View of the HIV Epidemic, *Bull Int. Union Tubercul. Lung Dis.* 66: 33–36 (1991).

Current drugs used for controlling mycobacteria other than *M. tuberculosis* are inadequate. Advisory Group for Opportunistic Disease Research and Education, 1992, Mastering Opportunistic Mycobacterial Infections, Parmitalia Carlo Erba, Barnet, Herts, United Kingdom. Furthermore, the recent increase of *tuberculosis* in the United States has been accompanied by the appearance of drug-resistant strains of *M. tuberculosis*. Bloom, B. R. and Murray, C. J. L., Tuberculosis: Commentary on a Reemergent Killer, *Science* 257: 1055–1064 (1992); Snider, D. E. and Roper, W. L., The New Tuberculosis, *N. Eng. J. Med.* 326: 703–705 (1992).

Accordingly, there exists a need for new drugs to combact mycobacteria and particularly *M. tuberculosis* and *M. avium-intracellulare*. The compounds of the present invention satisfy this need.

SUMMARY OF THE INVENTION

It is therefore an object of the present invention to provide a compound having the structure:

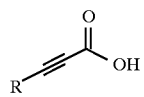

wherein R is a branched or unbranched C1–C30 alkyl, alkenyl or alkynl; or a branched or unbranched C1–C30 alkyl, alkenyl or alkynl substituted with S, O, N, P, SO$_2$, F, Cl, Br, or I, wherein S, O, N, P, or SO$_2$ replaces at least one —CH$_2$—, and F, Cl, Br, or I replaces at least one H.

It also is an object of the present invention to provide a pharmaceutical composition comprising the compound above and a pharmaceutically acceptable carrier.

Lastly, it is an object of the present invention to provide a method for treating a mycobacterial disease or infection in a subject in need of such treatment which comprises administering to the subject an amount of the compound above effective to treat the disease or infection.

DETAILED DESCRIPTION OF THE INVENTION

Figure 1:
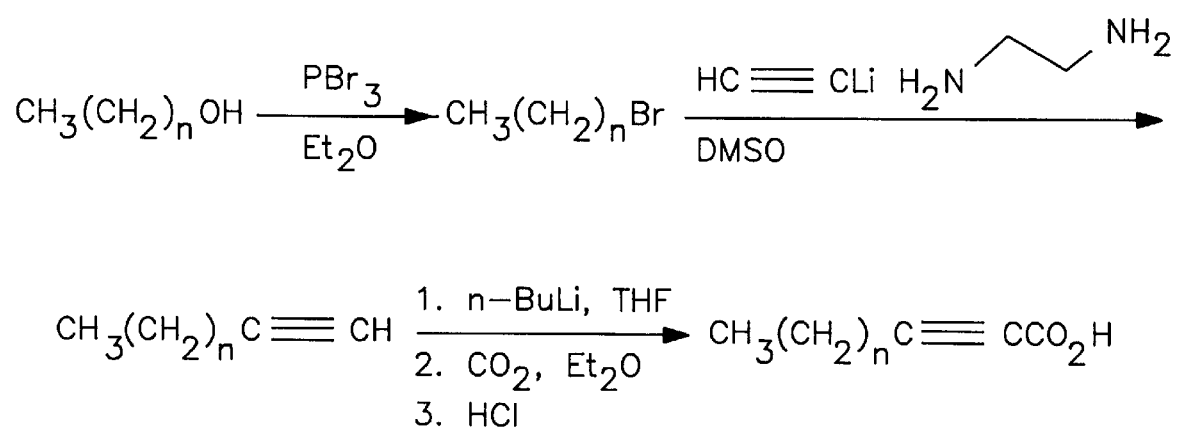
FIG. 1. Schematic diagram of the synthesis of the compounds of the present invention.

The present invention provides a novel class of "kynoylic acid (KOA)" compounds having the structure:

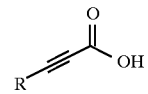

wherein R is a branched or unbranched C1–C30 alkyl, alkenyl or alkynl; or a branched or unbranched C1–C30 alkyl, alkenyl or alkynl substituted with S, O, N, P, SO$_2$, F, Cl, Br, or I, wherein S, O, N, P, or SO$_2$ replaces at least one —CH$_2$—, and F, Cl, Br, or I replaces at least one H.

In the preferred embodiment, R is an unbranched C9–C30 alkyl, and more preferrably, an unbranched C9–C20 alkyl. Such compounds include but are not limited to 2-dodecynoic acid (C12KOA, i.e. contains a total of 12 carbon atoms), 2-tetradecynoic acid (C14KOA), 2-hexadecynoic acid (C16KOA), 2-heptadecynoic acid (C17KOA), 2-octadecynoic acid (C18KOA), 2-nonadecynoic acid (C19KOA), 2-eicosynoic acid (C20KOA), 2-docosynoic acid (C22KOA), 2-tetracosynoic acid (C24KOA) and 2-pentacosynoic acid (C25KOA).

Suitable compounds also include but are not limited to compounds in which the alkyl chain is substituted with sulfur such as 13-(hexylthio)-2-tridecynoic acid, as well as compounds having an alkynl chain as the R group with a triple bond between carbons C2 and C3 (or between the fifth and sixth carbon positions if the carbonyl carbon atom is donoted as C1)), such as 2,5-octadecadiynoic acid and 2,5-nonadecadiynoic acid.

The compounds of the present invention may be present in the form of free bases or pharmaceutically acceptable acid addition salts thereof. Examples of suitable acids for salt formation are: methanesulfonic, sulfuric, hydrochloric, phosphoric, acetic, citric, lactic, ascorbic, maleic, and the like.

The present invention also provides a pharmaceutical composition comprising one or more of the compounds above and a pharmaceutically acceptable carrier. The carrier must be "acceptable" in the sense of being compatible with the other ingredients of the formulation and not deleterious to the recipient thereof. The compound may be formulated with one or more pharmaceutically acceptable diluents or carriers, and optionally, any other ingredients which may be therapeutic per se, and/or may be synergistic with the compounds of the present invention. These include chemotherapeutic agents known to act against the particular mycobacterial species (e.g. for *M. tuberculosis*, these compounds may include isoniazid, ethionamide, rifampicin and/or pyrazinamide). The concentration of the compound present in the formulation will depend upon the choice of carrier as well as the results desired.

Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The choice of carrier will depend upon the route of administration. The formulations may conveniently be presented in unit dosage and may be prepared by methods well-known in the pharmaceutical art, by bringing the active compound into association with a carrier or diluent, as a suspension or solution, and optionally one or more accessory ingredients, e.g. buffers, flavoring agents, surface active agents, and the like.

For parenteral administration (i.e., intravenous, intramuscular, subcutaneous, or intraperitoneal administration), the compound is combined with a sterile aqueous solution which is preferably isotonic with the blood of the recipient. Formulations suitable for such administration may conveniently comprise a sterile aqueous preparation of the active compound which is preferably made isotonic, and may be formulated by dissolving solid active ingredient in water containing physiologically compatible substances such as sodium chloride, glycine, and the like, and having a buffered pH compatible with physiological conditions to produce an aqueous solution, and rendering said solution sterile. Preparations for injections may also be formulated by suspending or emulsifying the compounds in non-aqueous solvent, such as vegetable oil, synthetic aliphatic acid glycerides, esters of higher aliphatic acids or propylene glycol. The formulations may be present in unit or multi-dose containers such as sealed ampoules or vials.

For oral administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

The present invention further provides a method for treating a mycobacterial disease or infection in a subject in need of such treatment which comprises administering to the subject an amount of the compound above effective to treat the mycobacterial disease or infection.

The term "treatment" includes the partial or total inhibition of mycobacterial disease or infection. The term "subject" includes a human or animal subject diagnosed as having the mycobacterial disease or infection. In the preferred embodiment, the mycobacterial disease is *M. tuberculosis* or *M. avium*, and most preferably is *M. tuberculosis*. The administration may be affected by means known to those skilled in the art such as oral, rectal, topical, intravenous, subcutaneous, intramuscular, or intraperitoneal routes of administration.

The dosage form and amount can be readily established by reference to known chemotherapeutic treatments of mycobacterial diseases or infections. In general, however, the dosage of the compound will be within the range of about 0.01 μg/kg to about 100 mg/kg, and preferably between about 1 μg/kg and about 10 mg/kg. The actual dose will depend upon the route of administration, the pharmacokinetic properties of the individual treated, as well as the results desired.

The present invention is described in the following examples which are set forth to aid in the understanding of the invention, and should not be construed to limit in any way the invention as defined in the claims which follow thereafter.

Example 1

Preparation of Compounds

The scheme for preparing the compounds of the present invention is outlined in FIG. 1. A detailed description of the synthesis of these compounds is as follows:

A. 1-Bromoalkanes

To a suspension of 1-hydroxyalkane (6.1 mmol) in dry ether (15 mL) was added, under nitrogen, phosphorus tribromide (580 mL, 6.1 mmol). The white suspension was heated at reflux for 3 h, and then stirred at room temperature overnight. The reaction mixture was quenched by addition of a saturated solution of sodium bicarbonate at 0° C. After the mixture was stirred for 30 min, the ether phase was separated, dried over sodium sulfate, filtered, evaporated under vacuum, and filtered through a pad of silica gel (elution with hexane) to give the 1-bromoalkane.

B. 1-Alkynes

A suspension of lithium acetylide ethylene-diamine complex (412 mg, 4.5 mmol) in dry dimethyl sulfoxide (2.2 mL) was stirred for 10 min at room temperature under nitrogen. After cooling to 8° C., 1-bromoalkane (4.1 mmol) was added dropwise (if the bromoalkane is a solid, it is solubilized first in tetrahydrofuran). The reaction mixture was stirred at room temperature for 4 h, and cooled to 0° C. Water (1 mL) was added very slowly. The suspension was stirred for 10 min at room temperature, then poured into water (60 mL), and extracted with hexane. The combined organic phases were dried over sodium sulfate, filtered, evaporated under vacuum, purified by filtration through a small pad of silica gel, eluted with hexane, and analyzed by $^1$H and $^{13}$C NMR.

C. 2-Alkynoic Acids

To a solution of 1-alkyne (1.63 mmol) in dry THF (6.5 mL), at −23° C., was added n-butyllithium (2.5M solution in hexanes, 0.69 mL, 1.73 mmol) under nitrogen. The solution was stirred for 1 h, cooled to −50° C., and then poured into a slurry of dry ice (3 g)/dry ether (3 mL). The reaction mixture was stirred at room temperature overnight, poured into 3N HCl, and extracted with ether. The combined organic phases were dried over sodium sulfate, filtered, evaporated under vacuum, and purified by flash chromatography (elution with hexane/ethyl acetate/glacial acetic acid 80/20/1).

D. 2,5-Alkadiynoic Acids, 5-Alkynoic Acids and Sulfer Containing 2-Alkynoic Acids 2,5-alkadiynoic acids were prepared by coupling alknylmagnesium bromides to propargyl bromide, and followed by carboxylation. 5-alkynoic acids were obtained by coupling ω-bromoalkanes with the lithium salt of 6-hexyn-1-ol (with the alcohol group protected as a tetrahydropyranyl ether) followed by oxidation to the acid function of the deprotected alcohol group. Sulfur-containing 2-alkynoic acids were prepared by condensation of alkyl thiols to dibromoalkanes, formation of the terminal alkynes by addition of the resulting ω-bromothioalkane to lithium acetylide-ethylenediamine complex, and then carboxylation by the usual procedure.

Example 2

Testing of Compounds

The CDC indirect proportion method of suseptibility testing was used to evaluate the activity of compounds C18KOA and C20KOA against *M. tuberculosis.* This method was performed with a bacterial suspension made from a fresh 7H9 broth culture. A suspension was adjusted to the optical density of a MacFarland Standard No. 1, and two dilutions of this suspension, $10^{-3}$ and $10^{-4}$, were then used to inoculate two separate sets of 7H10/OADC quadrant plates, one for each drug. Drug-free medium was placed in one quadrant of each set. The three other quadrants contained the drugs. For each respective dilution inoculum, three drops were placed in each quadrant, and the plates were incubated for two weeks at 37° C. in an atmosphere of 10% CO2. Plates were then read and the percentage of resistant bacteria in the population (1% or greater is defined as resistant) was reported on the basis of comparison of the number of colony-forming units (CFU) on the drug containing and drug-free quadrants found in the two sets of plates.

For the KOA compounds tested, four sets of plates were made which contained 0, 1, 10 and 100 μg/ml of either C18KOA or C20KOA. Defined bacterial suspensions of two *M. tuberculosis* strains (one is isoniazid susceptible and one is resistant) were inoculated on the plates, and the plates were incubated as described above. After two weeks, 100 to 200 CFU appeared on both *M. tuberculosis* strains on the C18KOA 0 and 1 μg/ml treated quadrants, but no CFU appeared on both *M. tuberculosis* strains on the 10 and 100 μg/ml quadrants. For C20KOA, 100 to 200 CFU appeared on both *M. tuberculosis* strains on the 0, 1, and 10 μg/ml treated quadrants, but no CFU appeared on both *M. tuberculosis* strains on the 100 μg/ml quadrant. In summary, C18KOA shows inhibitory antituberculosis activity of 10 μg/ml against isoniazid susceptible and resistant strains of *M. tuberculosis;* and C20KOA show inhibitory antituberculosis activity at 100 μg/ml against the same strains.

In separate tests using a macrobroth dilution assay, C12KOA, C14KOA, C16KOA, C17KOA, C18KOA, C19KOA, C20KOA and 13-(hexylthio)-2-tridecynoic acid also had activity against *M. smegmatis* as well as *M. tuberculosis,* and 2,5-nonadecadiynoic had activity against *M. smegnatis.* In addition, C16KOA and C18KOA was shown to have activity against *M. avium.*

All publications mentioned hereinabove are hereby incorporated in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for treating *M. avium* infection in a subject in need of said treatment which comprises administering to the subject an effective amount of a compound having the structure: $RC{\equiv}CCO_2H$, wherein R is an unbranched C9–C30 alkyl, to treat *M. avium* infection in the subject.

2. The method of claim 1, where R is a C15 alkyl.

* * * * *